(12) United States Patent
Oohara et al.

(10) Patent No.: US 10,111,892 B2
(45) Date of Patent: Oct. 30, 2018

(54) ANTI-CANCER AGENT

(75) Inventors: Nobuhiko Oohara, Tokyo (JP);
Kazuhiro Nakatsui, Tokyo (JP)

(73) Assignee: Nippon Chemical Industrial Co., Ltd., Tokyo (JP)

( * ) Notice: Subject to any disclaimer, the term of this patent is extended or adjusted under 35 U.S.C. 154(b) by 0 days.

(21) Appl. No.: 13/513,909

(22) PCT Filed: Dec. 20, 2010

(86) PCT No.: PCT/JP2010/072902
§ 371 (c)(1),
(2), (4) Date: Jun. 5, 2012

(87) PCT Pub. No.: WO2011/078122
PCT Pub. Date: Jun. 30, 2011

(65) Prior Publication Data
US 2012/0252762 A1    Oct. 4, 2012

(30) Foreign Application Priority Data
Dec. 21, 2009  (JP) ............... 2009-289663

(51) Int. Cl.
*A61K 31/495* (2006.01)
*A61K 31/675* (2006.01)
*C07F 9/6509* (2006.01)

(52) U.S. Cl.
CPC ...... *A61K 31/675* (2013.01); *C07F 9/650982* (2013.01)

(58) Field of Classification Search
CPC ............ A61K 31/675; C07F 9/650982
USPC ............ 514/85, 184, 249; 556/19, 110
See application file for complete search history.

(56) References Cited

U.S. PATENT DOCUMENTS

| | | | | |
|---|---|---|---|---|
| 5,843,993 | A * | 12/1998 | Katti et al. | 514/495 |
| 8,106,186 | B2 * | 1/2012 | Kodama et al. | 540/145 |
| 8,278,303 | B2 * | 10/2012 | Kodama et al. | 514/249 |
| 2009/0076267 | A1 * | 3/2009 | Kodama et al. | 544/225 |
| 2010/0048894 | A1 | 2/2010 | Kodama et al. | |

FOREIGN PATENT DOCUMENTS

| | | |
|---|---|---|
| JP | 2007-320909 A | 12/2007 |
| WO | WO-2007/139176 A1 | 12/2007 |

OTHER PUBLICATIONS

McKeage, Mark J. et al., "Anti tumor activity of gold (I), silver(I) and copper (I) complexes containing chiral tertiary phosphines", 1998, Metal-Based Drugs, 5(4), pp. 217-223.*
Brunner, Henri et al., "Stereochemical Exploitation of the Chiral (+)-9-Phenyldeltacyclanyl Substituent in Diphosphanes and Their Ni, Pd and Pt Complexes", Oct. 2002, Eur. J. Inorg. Chem., vol. 2002, Issue 10, pp. 2594-2602.*

International Search Report dated Feb. 22, 2011, issued for PCT/JP2010/072902.

* cited by examiner

Primary Examiner — My-Chau T. Tran
(74) Attorney, Agent, or Firm — Locke Lord LLP

(57) ABSTRACT

The anti-cancer agent of the present invention contains at least one kind of phosphine transition metal complex selected from a group of compounds represented by the following Formulae (1a) to (1d). According to this anti-cancer agent, an anti-cancer agent is provided which has a higher anti-cancer activity and lower toxicity compared to anti-cancer agents in the related art. In Formulae (1a), (1b), (1c), and (1d), $R^1$ and $R^2$ represent a linear or branched alkyl group, and $R^1$ has a higher priority than $R^2$ as ranked according to RS notation. $R^3$ and $R^4$ represent a hydrogen atom or a linear or branched alkyl group. M represents an atom of a transition metal selected from a group consisting of gold, copper, and silver. $X^-$ represents an anion.

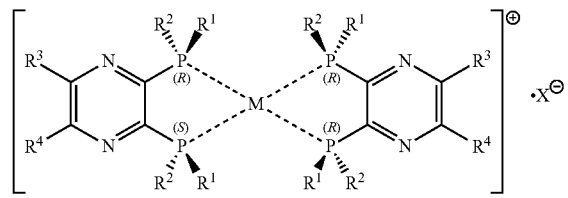

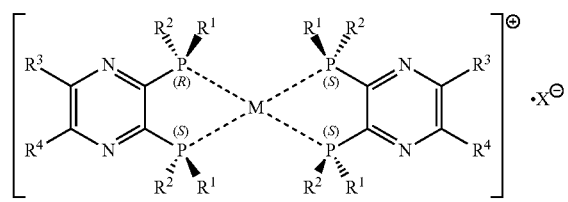

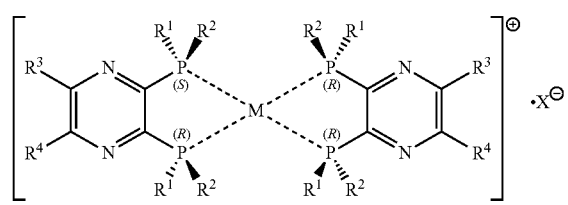

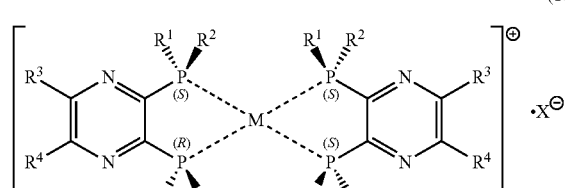

2 Claims, No Drawings

ANTI-CANCER AGENT

TECHNICAL FIELD

The present invention relates to an anti-cancer agent containing a phosphine transition metal complex.

BACKGROUND ART

The present applicant previously proposed an anti-cancer agent containing a phosphine transition metal complex represented by the following Formula (1') (see PTL 1). In the formula, $R^1$, $R^2$, $R^3$, and $R^4$ are alkyl groups or the like, and M is gold, copper, or silver. This anti-cancer agent has an anti-cancer activity higher than that of an anti-cancer agent such as cisplatin or Taxol (registered trademark) that has been used in the related art.

[Chem. 1]

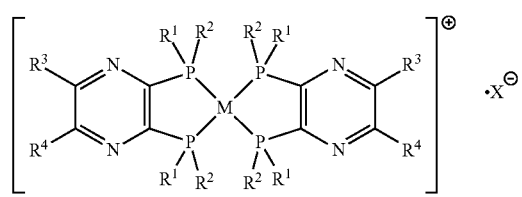

(1')

The above phosphine transition metal complex contains 4 asymmetric phosphorous atoms, so there are numerous isomers for this complex. PTL 1 discloses that the type of the isomers is not particularly limited, and that the steric structure of the phosphorous atoms may be constituted with a single enantiomer such as (R,R)(R,R) or (S,S)(S,S) or with racemic isomers of ligands such as (R,R)(S,S). PTL 1 also discloses that the steric structure may be constituted with meso isomers such as (R,S)(S,R) or with one enantiomer and a meso isomer thereof such as (R,R)(S,R).

CITATION LIST

Patent Literature

[PTL 1] JP-A-2007-320909

SUMMARY OF INVENTION

Technical Problem

Generally, it is known that the anti-cancer activity and the anti-cancer spectrum of a compound depend on the chemical structure of the compound, and that the efficacy of the compound varies from person to person. For example, though Taxol (registered trademark) described above is known as a highly active anti-cancer agent, the efficacy ratio thereof is about 30%. Therefore, the development of various novel anti-cancer agents having different chemical structures is desirable. In addition, the anti-cancer agents are required to have characteristics including a low toxicity as well as a high anti-cancer activity.

In consideration of the above circumstances, the present invention aims to improve the above-described anti-cancer agent proposed by the present applicant.

Solution to Problem

According to the present invention, there is provided an anti-cancer agent containing at least one kind of phosphine transition metal complex selected from a group of compounds represented by Formulae (1a) to (1d).

[Chem. 2]

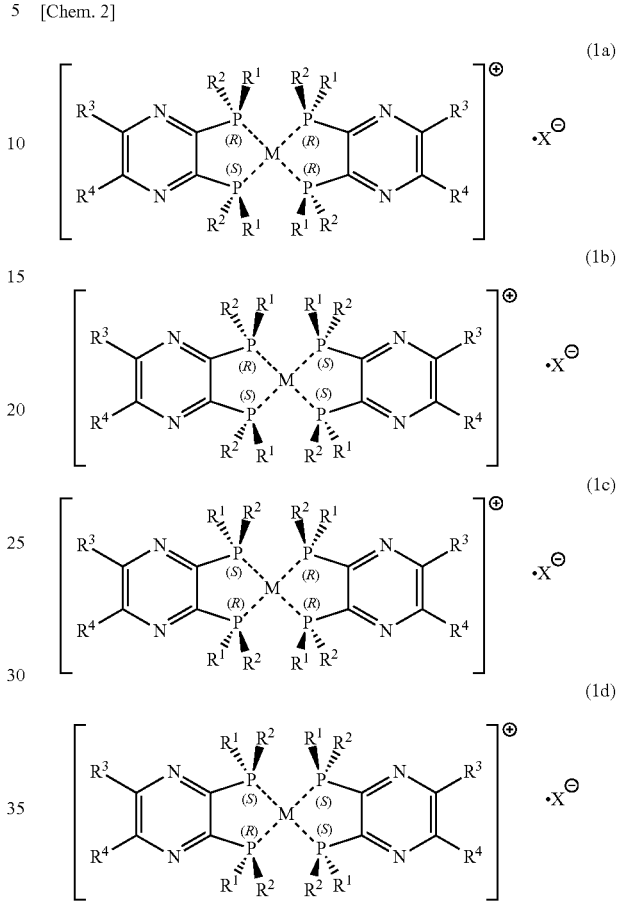

In the Formulae, $R^1$ and $R^2$ represent a linear or branched alkyl group, a cycloalkyl group, a cycloalkyl group having a substituent, an adamantyl group, a phenyl group, or a phenyl group having a substituent that has 1 to 10 carbon atoms. $R^1$ and $R^2$ are different from each other, and $R^4$ has a higher priority than $R^2$ as ranked according to RS notation. $R^3$ and $R^4$ represent a hydrogen atom or a linear or branched alkyl group having 1 to 6 carbon atoms, and may be groups that are the same as or different from each other. $R^3$ and $R^4$ may form a saturated or unsaturated ring by binding to each other, and the saturated or unsaturated ring may have a substituent. M represents an atom of a transition metal selected from a group consisting of gold, copper, and silver, and $X^-$ represents an anion.

Advantageous Effects of Invention

According to the present invention, an anti-cancer agent having a high anti-cancer activity and low toxicity is provided.

DESCRIPTION OF EMBODIMENTS

The anti-cancer agent of the present invention contains at least one kind phosphine transition metal complex selected from a group of compounds represented by the Formulae (1a) to (1d). This phosphine transition metal complex has a structure in which two ligands including a 2,3-bisphosphinopyrazine derivative are coordinated with respect to a central metal ion M. In the 2,3-bisphosphinopyrazine derivative, $R^1$ and $R^2$ are different groups, so two phosphorous atoms become a chiral center. Consequently, this 2,3-bisphosphinopyrazine derivative has three types of isomers including an (R,R) isomer, an (S,S) isomer, and an (R,S) isomer differing in a steric configuration. Therefore, the compounds represented by Formulae (1a) to (1d) are isomers differing in steric configuration. As described above in the section of Background Art, the phosphine transition metal complex represented by (1') that includes Formulae (1a) to (1d) has numerous isomers differing in steric configuration. The present inventors conducted thorough study, and as a result, they found that by using compounds represented by Formulae (1a) to (1d) among those isomers, it is possible to obtain an anti-cancer agent having a higher anti-cancer activity and lower toxicity compared to the anti-cancer agent disclosed in PTL 1.

It has not been completely clarified why the compounds represented by Formulae (1a) to (1d) have a higher anti-cancer activity and low toxicity. However, the present inventors consider that this might be because the anti-cancer activity and the anti-cancer spectrum of an anti-cancer agent depend heavily on the chemical structure of the anti-cancer agent. For example, though the following compound represented by (1a') is included in the compound represented by the compound (1') disclosed in PTL 1, the toxicity of the compound (1a') is relatively high, which has been confirmed as a result of the study of the present inventors (see Comparative Example 1 described later).

[Chem. 3]

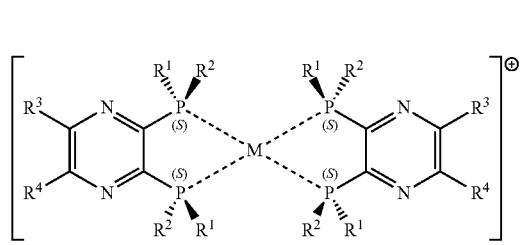

(1a')

In the formula, $R^1$, $R^2$, $R^3$, $R^4$, M, and $X^-$ have the same definition as described above.

The compounds represented by Formulae (1a) to (1d) may be used alone or used in combination of two or more kinds thereof. As a result of the study of the present inventors, it was confirmed that it is more advantageous to use the compounds represented by the Formulae (1a) to (1d) in combination of two or more kinds thereof than to use the compounds alone, in view of further reducing toxicity. Particularly, it was confirmed that if all of the compounds represented by Formulae (1a) to (1d) are used in combination, a high anti-cancer activity is demonstrated, and the toxicity is greatly reduced.

When all of the compounds represented by Formulae (1a) to (1d) are used in combination, the mixing ratio (molar ratio) of the four compounds is not particularly critical. For example, the mixing ratio can be set to (1a):(1b):(1c):(1d)=10 to 90:10 to 90:10 to 90:10 to 90, and particularly set to 20 to 40:20 to 40:20 to 40:20 to 40. If the four kinds of compounds are used in combination within this range of the molar ratio, it is possible to further reduce the toxicity. In current HPLC techniques, the compounds represented by Formulae (1a) to (1d) cannot be separated. However, according to the production method described later, it is considered that the product thereof contains the compounds represented by Formulae (1a) to (1d) in the above molar ratio.

The anti-cancer agent of the present invention may contain at least one kind of phosphine transition metal complex selected from a group of compounds represented by the following Formulae (2a) to (2c), in addition to the compounds represented by Formulae (1a) to (1d). If the compounds represented by Formulae (2a) to (2c) are concurrently used, it is possible to further reduce the toxicity of the anti-cancer agent of the present invention.

[Chem. 4]

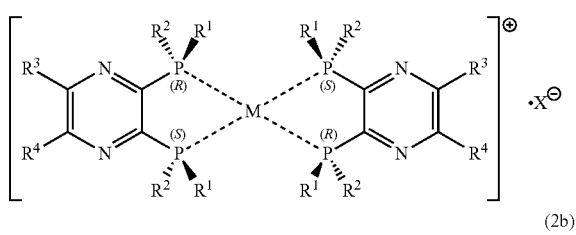

(2a)

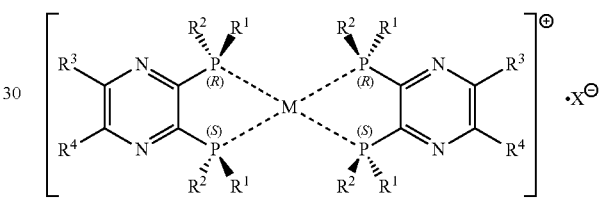

(2b)

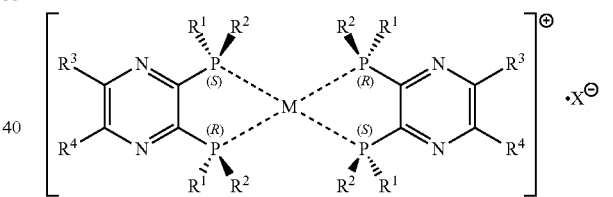

(2c)

In the Formulae, $R^1$, $R^2$, $R^3$, $R^4$, M, and $X^-$ have the same definition as described above.

The compounds represented by Formulae (2a) to (2c) may be used alone or used in combinations of two or more kinds thereof. As a result of the study of the present inventors, it was confirmed that it is more advantageous to use the compounds represented by the Formulae (2a) to (2c) in combinations of two or more kinds thereof than to use the compounds alone, in view of further reducing toxicity. Particularly, it was confirmed that if all of the compounds represented by Formulae (2a) to (2c) are used in combination, the toxicity is further reduced.

When the compounds represented by Formulae (2a) to (2c) are used in combination of two or more kinds thereof, the mixing ratio (molar ratio) of the two kinds of compounds is preferably from 25/75 to 75/25, and particularly preferably from 40/60 to 60/40 in any combination. If the two kinds of compounds are used in combination within this range of the molar ratio, it is possible to further reduce the toxicity.

When all of the compounds represented by Formulae (2a) to (2c) are used in combination, the mixing ratio (molar ratio) of the three compounds is not particularly critical. For example, the mixing ratio can be set to (2a):(2b):(2c)=10 to 40:20 to 80:10 to 40, and particularly set to 20 to 30:40 to 60:20 to 30. If the three kinds of compounds are used in combination within this range of the molar ratio, it is possible to further reduce the toxicity. In current HPLC techniques, the compounds represented by Formulae (2a) to (2c) cannot be separated. However, according to the production method described later, it is considered that the product thereof contains the compounds represented by Formulae (2a) to (2c) in the above molar ratio.

When the compounds represented by Formulae (1a) to (1d) are used concurrently with the compounds represented by Formulae (2a) to (2c), the molar ratio (the former:the latter) between the total amount of the compounds represented by Formulae (1a) to (1d) and the total amount of the compounds represented by Formulae (2a) to (2c) is preferably 10 to 90:90 to 10, and particularly preferably 50 to 80:20 to 50, in view of reducing the toxicity.

The anti-cancer agent of the present invention may contain a phosphine transition metal complex represented by the following Formula (3), in addition to the compounds represented by Formulae (1a) to (1d). If the compound represented by Formula (3) is concurrently used, it is also possible to further reduce the toxicity of the anti-cancer agent of the present invention.

[Chem. 5]

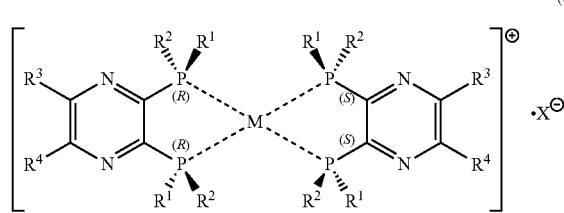

(3)

In the formulae, $R^1$, $R^2$, $R^3$, $R^4$, M, and $X^-$ have the same definition as described above.

When the compounds represented by Formulae (1a) to (1d) are used concurrently with the compound represented by Formula (3), the molar ratio (the former:the latter) between the total amount of the compounds represented by Formulae (1a) to (1d) and the compound represented by Formula (3) is preferably 10 to 90:90 to 10, and particularly preferably 50 to 80:20 to 50, in view of reducing the toxicity.

In the anti-cancer agent of the present invention, the compounds represented by Formulae (1a) to (1d), the compounds represented by Formulae (2a) to (2c), and the compound represented by Formula (3) may be used in combination. If the three kinds of compounds are used in combination, it is also possible to demonstrate a high anti-cancer activity and to further reduce the toxicity. When the three types of compounds are used in combination, the mixing ratio (molar ratio) between the total amount of the compounds represented by Formulae (1a) to (1d), the total amount of the compounds represented by Formulae (2a) to (2c), and the compound represented by Formula (3) is preferably set to Formulae (1a) to (1d):Formulae (2a) to (2c):Formula (3)=20 to 80:10 to 30:10 to 80, and particularly preferably set to 40 to 70:5 to 25:15 to 50.

It is desirable that the anti-cancer agent of the present invention do not contain the compound represented by Formula (1a') as far as possible. However, it is inevitable that a small amount (for example, 10 mol % or less of the total amount) of the compound represented by Formula (1a') is contained in the anti-cancer agent.

In the Formulae (1a) to (1d), Formulae (2a) to (2c), and Formula (3), $R^1$ and $R^2$ represent a linear or branched alkyl group, a cycloalkyl group, a cycloalkyl group having a substituent, an adamantyl group, a phenyl group, or a phenyl group having a substituent. $R^1$ and $R^2$ have 1 to 10 carbon atoms, and are groups different from each other. In addition, between $R^1$ and $R^2$, $R^1$ is a group that has a higher priority than $R^2$ as ranked according to RS notation.

Examples of the alkyl group represented by $R^1$ and $R^2$ include a methyl group, an ethyl group, an isopropyl group, an n-propyl group, an isobutyl group, an n-butyl group, a sec-butyl group, a tert-butyl group, an isoheptyl group, an n-heptyl group, an isohexyl group, and an n-hexyl group. Examples of the cycloalkyl group represented by $R^1$ and $R^2$ include a cyclopentyl group and a cyclohexyl group. When $R^1$ and $R^2$ are a cycloalkyl group having a substituent or a phenyl group having a substituent, examples of the substituent include an alkyl group, a nitro group, an amino group, a hydroxyl group, a fluoro group, a chloro group, a bromo group, an iodo group, and the like. Particularly, $R^1$ is preferably a tert-butyl group or an adamantyl group, and $R^2$ is preferably a methyl group, in view of enhancing the anti-cancer activity.

$R^3$ and $R^4$ represent a hydrogen atom or a linear or branched alkyl group, and the alkyl group represented by $R^3$ and $R^4$ has 1 to 6 carbon atoms. $R^3$ and $R^4$ may be groups that are the same as or different from each other. When $R^3$ and $R^4$ form a saturated or unsaturated ring by binding to each other, the saturated or unsaturated ring may have a substituent.

Examples of the alkyl group represented by $R^3$ and $R^4$ include an ethyl group, an isopropyl group, an n-propyl group, an isobutyl group, an n-butyl group, a sec-butyl group, a tert-butyl group, an isoheptyl group, an n-heptyl group, an isohexyl group, an n-hexyl group, a cyclopentyl group, a cyclohexyl group, and the like.

When $R^3$ and $R^4$ form a saturated or unsaturated ring by binding to each other, examples of the ring include saturated or unsaturated 5-membered or 6-membered rings. Examples of such rings include a phenyl group, a cyclohexyl group, a cyclopentyl group, and the like. The ring may have a monovalent substituent, and examples of the substituent include a linear or branched alkyl group having 1 to 5 carbon atoms, a nitro group, an amino group, a hydroxyl group, a fluoro group, a chloro group, a bromo group, and an iodo group.

Particularly, it is preferable that $R^3$ and $R^4$ form a benzene ring by binding to each other, in view of enhancing the anti-cancer activity. In this case, a ligand coordinated to a metal M becomes a quinoxaline derivative. In the benzene ring in this quinoxaline derivative, at least one of four hydrogen atoms may be substituted with the above-described substituent.

M represents a monovalent transition metal atom selected from a group consisting of gold, copper, and silver. Particularly, M is preferably a gold atom in view of enhancing the anti-cancer activity.

$X^-$ represents an anion, and examples of the anion include a chlorine ion, a bromine ion, an iodine ion, a tetrafluoroborate ion, a hexafluorophosphate ion, a perchloric acid ion, and the like. Among these, a chlorine ion, a bromine ion, and an iodine ion are preferable as $X^-$, in view of enhancing the anti-cancer activity.

Next, a preferable method of producing the phosphine transition metal complex contained in the anti-cancer agent of the present invention will be described. The phosphine transition metal complex is obtained by causing a reaction between a 2,3-bisphosphinopyrazine derivative represented by Formula (4) and a salt of gold, copper, or silver.

[Chem. 6]

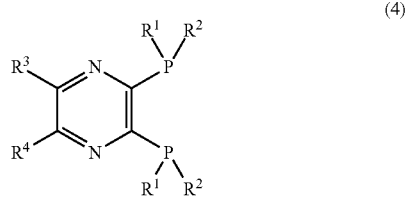

(4)

In the formula, $R^1$, $R^2$, $R^3$, and $R^4$ have the same definition as described above.

The 2,3-bisphosphinopyrazine derivative represented by Formula (4) is produced by, for example, causing a reaction between 2,3-dichloropyrazine (6) and phosphine-borane (7) to obtain bis(phosphine-borane)pyrazine (8) and then causing a deboranation reaction of the obtained bis(phosphine-borane)pyrazine (8), as shown in a Reaction Formula (9).

[Chem. 7]

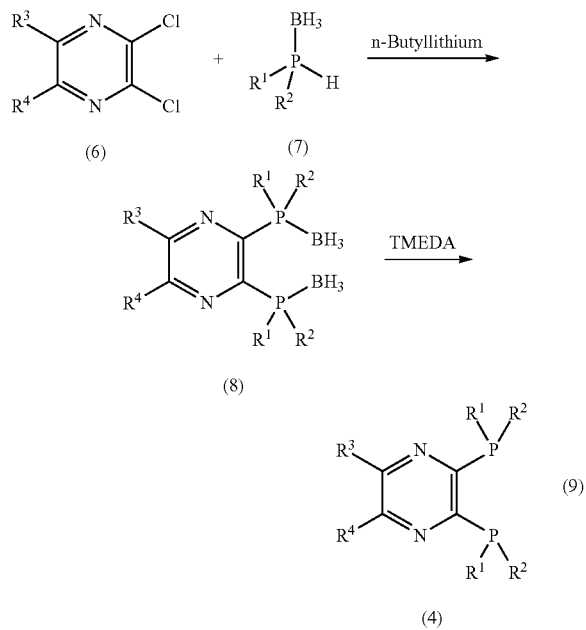

In the formula, $R^1$, $R^2$, $R^3$, and $R^4$ have the same definition as described above.

In the Reaction Formula (9), for example, the 2,3-dichloropyrazine (6) and the phosphine-borane (7) are allowed to react at −78° C. to 30° C. for 1 to 24 hours in the presence of a base such as n-butyllithium, in an inert solvent such as tetrahydrofuran or N,N-dimethylformamide.

The 2,3-dichloropyrazine (6) and the phosphine-borane (7) are produced by known methods, and the 2,3-dichloropyrazine (6) is commercially available. The phosphine-borane (7) is produced by, for example, methods disclosed in JP-A-2003-300988, JP-A-2001-253889, J. Org. Chem. 2000, Vol. 65, P 4185-4188, and the like.

The deboranation reaction of the bis(phosphine-borane) pyrazine (8) is carried out at 0° C. to 100° C. for 10 minutes to 3 hours by adding a deboranating agent such as N,N,N'N'-tetramethylethylenediamine (TMEDA) in a reaction system containing the bis(phosphine-borane)pyrazine (8).

In the 2,3-bisphosphinopyrazine derivative represented by Formula (4), $R^1$ and $R^2$ are different groups, so two phosphorous atoms become a chiral center. Consequently, this 2,3-bisphosphinopyrazine derivative has 3 types of isomers including an (R,R) isomer, an (S,S) isomer, and an (R,S) isomer differing in a steric configuration. Among these 3 types of isomers, the (R,S) isomer is a meso isomer, and an equimolar mixture of the (R,R) and (S,S) isomers becomes racemic isomers. If these 3 types of isomers are used in an appropriate amount, it is possible to obtain a phosphine transition metal complex having a target steric structure.

For example, if a mixture of the (R,S) isomer, that is, a meso isomer and racemic isomers of the (R,R) and (S,S) isomers is used as the 2,3-bisphosphinopyrazine derivative, a mixture of a phosphine transition metal complex including 4 types of the compounds represented by Formulae (1a) to (1d), a phosphine transition metal complex including 3 types of the compounds represented by Formulae (2a) to (2c), and a phosphine transition metal complex represented by Formula (3) is obtained.

In addition, if the (R,S) isomer, that is, a meso isomer is used as the 2,3-bisphosphinopyrazine derivative, a phosphine transition metal complex including 3 types of the compounds represented by Formulae (2a) to (2c) is obtained. Moreover, if racemic isomers of the (R,R) isomer and the (S,S) isomer are used, a phosphine transition metal complex including the compound represented by Formula (3) is obtained.

The mixture of a meso isomer and racemic isomers can be obtained by using racemic isomers of the R isomer and the S isomer as the phosphine-borane (7) in the Reaction Formula (9). In this case, if the composition of these is adjusted by using a mixed solvent of two or more kinds of inert solvents in the Reaction Formula (9), it is possible to control the ratio of the meso isomer and the racemic isomers generated. As the mixed solvent, for example, it is possible to use a combination of tetrahydrofuran and N,N-dimethylformamide.

For the 2,3-bisphosphinopyrazine derivative of the (R,S) isomer, if the obtained mixture of the meso isomer and the racemic isomers is separated by chromatography, the meso isomer (that is, the (R,S) isomer) is separated from the racemic isomers (that is, the (R,R) isomer and the (S,S) isomer), whereby the (R,S) isomer can be isolated. The racemic isomers, that is, the (R,R) isomer and the (S,S) isomer are not separated from each other.

The 2,3-bisphosphinopyrazine derivative of the (R,R) isomer can be obtained according to, for example, the method disclosed in Example 1 of JP-A-2007-56007 relating to the previous application of the present applicant.

The salt of gold, copper, or silver reacting with the 2,3-bisphosphinopyrazine derivative represented by Formula (4) is, for example, a halide, a nitric acid salt, a perchloric acid salt, a tetrafluoroborate salt, a hexafluorophosphate salt, or the like of those metals. In addition, these metals are monovalent metals. The salt of these metals may consist of two or more kinds of salts differing in any or both of metal and anion.

Examples of preferable transition metal salts of gold include gold(I) acid chlorate, gold(I) chloride, tetrabutylammonium chloride/gold(I) chloride, and the like ("Experimental Chemistry Course 21, Fifth Edition", edited by The Chemical Society of Japan, published by MARUZEN Co., Ltd., Mar. 30, 2004, pp 366-380, see pp 775-778 in Aust. J. Chem., 1997, 50). Examples of preferable transition metal salts of copper include copper(I) chloride, copper(I) bromide, copper(I) iodide, and the like ("Experimental Chemistry Course 21, Fifth Edition", edited by The Chemical Society of Japan, published by MARUZEN Co., Ltd., Mar. 30, 2004, pp 349-361). Examples of preferable transition metal salts of silver include silver(I) chloride, silver(I) bromide, silver(I) iodide, and the like ("Experimental Chemistry Course 21, Fifth Edition", edited by The Chemical Society of Japan, published by MARUZEN Co., Ltd., Mar. 30, 2004, pp 361-366). The transition metal salt relating to the method of producing the phosphine transition metal complex of the present invention may be an anhydride or a hydrated substance.

The molar ratio of the 2,3-bisphosphinopyrazine derivative represented by Formula (4) to the salt of gold, copper, or silver is preferably from 1 fold to 5 fold in terms of moles, and more preferably from 1.8 fold to 2.2 fold in terms of moles. The reaction can be carried out in a solvent such as acetone, acetonitrile, methanol, ethanol, tetrahydrofuran, dichloromethane, or chloroform. The reaction temperature is preferably from −20° C. to 60° C. and more preferably from 0° C. to 25° C., and the reaction time is preferably from 0.5 hours to 48 hours, and more preferably from 1 hour to 3 hours. By this reaction, the phosphine transition metal complex represented by Formulae (1a) to (1d), by Formulae (2a) to (2c), or by the Formula (3) is obtained. After the reaction ends, it is possible to optionally purify the complex by common methods.

The anion in the phosphine transition metal complex represented by Formulae (1a) to (1d), by Formulae (2a) to (2c), or by Formula (3) obtained in this manner may be converted into other desired anions. For example, first, a phosphine transition metal complex in which $X^-$ in Formulae (1a) to (1d), in Formulae (2a) to (2c), or in Formula (3) is a halide ion may be synthesized according to the production method described above, and then the phosphine transition metal complex may be reacted with an inorganic acid, an organic acid, or an alkali metal salt having a desired anion in an appropriate solvent, whereby it is possible to obtain a phosphine transition metal complex in which $X^-$ is a desired anion. Details of such a method are disclosed in, for example, JP-A-10-147590, JP-A-10-114782, and JP-A-61-10594.

The phosphine transition metal complex obtained in this manner is used as an anti-cancer agent. Types of cancer to which the anti-cancer agent of the present invention is applied are not particularly limited. Examples of the types of cancer include malignant melanoma, malignant lymphoma, digestive system cancer, lung cancer, esophageal cancer, stomach cancer, colorectal cancer, rectal cancer, colon cancer, ureteral tumor, gallbladder cancer, cholangiocarcinoma, biliary tract cancer, breast cancer, liver cancer, pancreatic cancer, testicular tumor, maxillary cancer, tongue cancer, cheilocarcinoma, oral cancer, pharyngeal cancer, laryngeal cancer, ovarian cancer, uterine cancer, prostate cancer, thyroid cancer, brain tumor, Kaposi's sarcoma, hemangioma, leukemia, polycythemia vera, neuroblastoma, retinoblastoma, myeloma, bladder tumor, sarcoma, osteosarcoma, myosarcoma, skin cancer, basal cell carcinoma, skin appendage cancer, cutaneous metastatic cancer, cutaneous melanoma, and the like. In addition, the anti-cancer agent can be applied not only to malignant tumors but also to benign tumors. The anti-cancer agent of the present invention can also be used for inhibiting metastasis of cancer, and particularly, the anti-cancer agent is useful as an inhibitor for postoperative metastasis of cancer.

The anti-cancer agent of the present invention can concurrently use a cyclodextrin compound so as to improve the solubility. Examples of the cyclodextrin compound include α-cyclodextrin, β-cyclodextrin, γ-cyclodextrin, methyl-β-cyclodextrin, dimethyl-β-cyclodextrin, trimethyl-β-cyclodextrin, 2-hydroxypropyl-β-cyclodextrin, 2-hydroxypropyl-α-cyclodextrin, dihydroxypropyl-β-cyclodextrin, hydroxyethyl-β-cyclodextrin, carboxymethyl-β-cyclodextrin, monoacetyl-β-cyclodextrin, 2-hydroxypropyl-γ-cyclodextrin, glucosyl-β-cyclodextrin, maltosyl-α-cyclodextrin, maltosyl-β-cyclodextrin, partial-methyl-β-cyclodextrin, α-cyclodextrin sulfate, β-cyclodextrin sulfate, and the like.

The anti-cancer agent of the present invention can be used in various forms by being administered to human beings or animals. The form of administration may be oral administration or parenteral administration such as intravenous injection, intramuscular injection, subcutaneous injection, intracutaneous injection, intrarectal administration, or transmucosal administration. Examples of the forms of preparations applied to oral administration include a tablet, a round pill, granules, powder, a capsule, a liquid, a suspension, an emulsion, a syrup, and the like. Examples of medicinal compositions applied to parenteral administration include an injectable solution, drops, nasal drops, a spray, an inhalation, a suppository, and a percutaneous absorbent such as an ointment, a cream, a powdery liniment, a liquid liniment, a patch, and the like. Examples of the form of the preparations of the anti-cancer agent of the present invention also include pellets for implantation and long acting preparations using known techniques.

Among the above, a physician appropriately selects preferable forms of administration, preparations, and the like according to a patient's age, sex, constitution, symptoms, stage of treatment, and the like.

When the anti-cancer agent of the present invention is a solid preparation such as a tablet, a round pill, powder, a dust formulation, or granules, these solid preparations are produced by mixing the phosphine transition metal complex represented by Formulae (1a) to (1d), by Formulae (2a) to (2c), or by the Formula (3) with appropriate additives, according to common methods. The additives include, for example, excipients such as lactose, sucrose, D-mannitol, corn starch, synthetic or natural gum, and crystalline cellulose; binders such as starch, hydroxypropyl cellulose, hydroxypropyl methyl cellulose, gum arabic, gelatin, and polyvinyl pyrrolidone; disintegrants such as calcium carboxymethyl cellulose, sodium carboxymethyl cellulose, starch, corn starch, and sodium alginate; lubricants such as talc, magnesium stearate, and sodium stearate; fillers such as calcium carbonate, sodium carbonate, calcium phosphate, and sodium phosphate; diluents, and the like. The tablet and the like may optionally be enteric-coated or coated with sugar, gelatin, or a film by using coating agents such as hydroxypropyl methyl cellulose, white sugar, polyethylene glycol, and titanium oxide.

When the anti-cancer agent of the present invention is a liquid preparation such as an injectable solution, eye drops, nasal drops, an inhalation, a spray, a lotion, a syrup, a liquid, a suspension, or an emulsion, in order to prepare these liquid preparations, the phosphine transition metal complex represented by Formulae (1a) to (1d), by Formulae (2a) to (2c) or Formula (3) is dissolved in an appropriate buffer such as purified water or a phosphoric acid buffer; a solution of physiological salts such as a physiological saline, Ringer's solution, or Locke's solution; vegetable oil such as cacao butter, sesame oil, or olive oil; and an organic solvent such as mineral oil, a higher alcohol, a higher fatty acid, or ethanol. Optionally, an emulsifier such as cholesterol; a suspension agent such as gum arabic; a dispersion aid; an infiltration agent; a surfactant such as a polyoxyethylene hydrated castor oil-based surfactant or a polyoxyethylene glycol-based surfactant; a dissolution aid such as sodium phosphate; a stabilizer such as sugar, a sugar alcohol, or albumin; a preservative such as paraben; a tonicity agent such as sodium chloride, glucose, or glycerin; a buffer; a soothing agent; an anti-adsorption agent; a moisturizer; an antioxidant; a colorant; a sweetener; a flavor; an aromatic substance; and the like may be added to the above solution. In this manner, the anti-cancer agent is prepared as a sterilized aqueous solution, a non-aqueous solution, a suspension, a liposome, an emulsion, or the like. At this time, it is particularly preferable for the injectable solution to have a physiological pH ranging from 6 to 8.

When the anti-cancer agent of the present invention is a semi-solid preparation such as a lotion, a cream, or an ointment, these semi-solid preparations are produced by appropriately mixing the phosphine transition metal complex represented by General Formula (1) with fat, fatty oil, lanoline, vaseline, paraffin, wax, a plaster, a resin, a plastic, glycols, a higher alcohol, glycerin, water, an emulsifier, a suspension agent, and the like.

The amount of the phosphine transition metal complexes represented by Formulae (1a) to (1d), Formulae (2a) to (2c), and Formula (3) contained in the anti-cancer agent of the present invention varies with the form of administration, seriousness, a dose to be administered, or the like. However, generally, the ratio of the total amount of the phosphine transition metal complexes represented by Formulae (1a) to (1d), Formulae (2a) to (2c), and Formula (3) to the total mass of the anti-cancer agent is preferably from 0.001% by mass to 80% by mass, and more preferably from 0.1% by mass to 50% by mass.

The dose of the anti-cancer agent of the present invention is appropriately determined by a physician according to, for example, conditions such as a patient's age, sex, body weight and symptoms, and the route of administration. However, generally, the daily dose for an adult ranges from about 1 µg/kg to about 1,000 mg/kg and preferably ranges from about 10 µg/kg to about 10 mg/kg, in terms of the amount of active ingredients. In this dosage range, the anti-cancer agent can be administered once a day or administered in several separate doses (for example, two to four times a day).

The anti-cancer agent of the present invention can also be used in combination with known chemotherapies, surgical therapies, radiotherapies, hyperthermia, immunotherapies, and the like.

EXAMPLES

The present invention will be described below in more detail based on examples, but the scope of the present invention is not limited to such examples. In the following description, "%" means "% by weight" unless otherwise specified.

Example 1

(1) Synthesis of mixture of (R,S)-2,3-bis(tert-butyl-methylphosphino)quinoxaline (meso isomer) and racemic isomers of (R,R)-2,3-bis(tert-butylmethyl-phosphino)quinoxaline and (S,S)-2,3-bis(tert-butyl-methylphosphino)quinoxaline Potassium-tert-butoxide (750 mmol) 84.2 g and 375 ml of dehydrated THF were added to a 1 L four-neck flask from which moisture had been sufficiently removed and which had been purged with nitrogen gas. This mixture was cooled to 0° C. in an ice bath, and 177.0 g (900 mmol) of a 60% THF solution of racemic-tert-butylmethyl phosphine borane was added dropwise thereto, followed by stirring for 30 minutes. A mixed solution containing 59.7 g (300 mmol) of 2,3-dichloroquinoxaline, 300 ml of dehydrated THF, and 75 ml of dehydrated DMF was added to a 3 L four-neck flask from which moisture had been sufficiently removed and which had been purged with nitrogen gas, followed by cooling to −10° C. The initially synthesized phosphine-borane solution was added dropwise thereto, followed by stirring for an hour. Thereafter, 139.4 g (1200 mmol) of tetramethylethylenediamine was added thereto, and the temperature thereof was returned to room temperature, followed by stirring for 3 hours. Hydrochloric acid (10%) was added dropwise thereto at 600 g to quench the resultant, followed by liquid separation, and then the resultant was washed with 150 g of 5% hydrochloric acid and then with 300 g of 2.5% aqueous sodium bicarbonate. In addition, 200 ml of hexane was added thereto, and the resultant washed with 150 ml of pure water. The obtained organic layer was dried, and then 300 ml of methanol was added thereto at 40° C., followed by stirring for an hour. The produced solid was filtered, thereby obtaining 69.9 g of orange-colored solid 2,3-bis(tert-butyl-methylphosphino)quinoxaline (yield 69.7%). The identification data was as follows.

$^{31}$P-NMR (CDCl$_3$); racemic isomers: −18.1, meso isomer: −15.4

HPLC (column Cosmosil 5C18-MS-II 4.6×250 mm, mobile phase methanol, flow rate 0.5 ml/min, temperature 30° C., UV 254 nm, elution time: racemic isomers 15 minutes, meso isomer 17 minutes), molar ratio of racemic isomer:meso isomer=52:48

(2) Synthesis of bis(2,3-bis(tert-butylmethylphos-phino)quinoxaline)gold(I) chloride In a 500 ml two-neck flask purged with nitrogen gas, 5.50 g (16.4 mmol) of the 2,3-bis(tert-butylmethylphosphino) quinoxaline obtained in the above manner and having a molar ratio of racemic isomers:meso isomer of 52:48 was dissolved in 220 ml of general-purpose THF. Tetrabutylammonium gold dichloride (8.2 mmol) was added thereto at 4.19 g, followed by stirring at room temperature for 5 hours. The produced brown sediment was filtered and then dissolved in 42 ml of dichloromethane, followed by washing with 50 ml of water, and the resultant was dried over sodium sulfate. The resultant was filtered, and then the solution was dried. The solid was dissolved in 50 ml of dichloromethane, and 270 ml of diethyl ether was added thereto. When the resultant was cooled to 0° C., a sold was precipitated, thereby obtaining 6.60 g of bis(2,3-bis(tert-butylmethyl-phosphino)quinoxaline)gold(I) chloride (yield 89.2%). This compound contained the compounds represented by Formulae (1a) to (1d) at 54 mol % in total, the compounds represented by Formulae (2a) to (2c) at 16 mol % in total, and the compound represented by Formula (3) at 22 mol % in total. This compound also contained the compound corresponding to (1a') at 8 mol %.

$^{31}$P-NMR (CDCl$_3$); 7.6-9.6 (m), 10.2 (s), 11.6-13.1 (m), 13.6 (s), 14.6-15.9 (m)

HPLC (column Sumichiral OA-8000 4.6×250 mm, mobile phase hexane:ethanol:methanol:trifluoroacetic acid=930:40:30:1, flow rate 1.0 ml/min, temperature 35° C., UV 254 nm, elution time: compounds represented by Formulae (2a) to (2c) 42 minutes, compounds represented by Formulae (1a) to (1d) 52 minutes, compound represented by Formula (1a') 56 minutes, compound represented by Formula (3) 61 minutes)

Example 2

A mixture of (R,S)-2,3-bis(tert-butylmethylphosphino)quinoxaline (meso isomer) and racemic isomers of (R,R)-2,3-bis(tert-butylmethylphosphino)quinoxaline and (S,S)-2,3-bis(tert-butylmethylphosphino)quinoxaline was synthesized in the same manner as in Example 1, except that the amount of dehydrated THF was set to 670 ml, and the amount of dehydrated DMF was set to 80 ml in the step (1) of Example 1. The molar ratio of racemic isomers:meso isomer was 54:46. Bis(2,3-bis(tert-butylmethylphosphino)quinoxaline) gold(I) chloride was obtained in the same manner as in Example 1 except for the molar ratio. This compound contained the compounds represented by Formulae (1a) to (1d) at 60 mol % in total, the compounds represented by Formulae (2a) to (2c) at 9 mol % in total, and the compound represented by Formula (3) at 26 mol % in total. This compound also contained the compound corresponding to Formula (1a') at 5 mol %. The ratio between the respective compounds was determined in the same manner as in the HPLC analysis method used in the synthesis of bis(2,3-bis(tert-butylmethylphosphino)quinoxaline)gold(I) chloride disclosed in the Example 1.

$^{31}$P-NMR (CDCl$_3$); 7.6-9.6 (m), 10.2 (s), 11.6-13.1 (m), 13.6 (s), 14.6-15.9 (m)

Example 3

A mixture of (R,S)-2,3-bis(tert-butylmethylphosphino)quinoxaline (meso isomer) and racemic isomers of (R,R)-2,3-bis(tert-butylmethylphosphino)quinoxaline and (S,S)-2,3-bis(tert-butylmethylphosphino)quinoxaline was synthesized in the same manner as in Example 1, except that the amount of dehydrated THF was set to 700 ml, and the amount of dehydrated DMF was set to 50 ml in the step (1) of Example 1. The molar ratio of racemic isomers:meso isomer was 44:56. Bis(2,3-bis(tert-butylmethylphosphino)quinoxaline)gold(I) chloride was obtained in the same manner as in Example 1 except for the molar ratio. This compound contained the compounds represented by Formulae (1a) to (1d) at 62 mol % in total, the compounds represented by Formulae (2a) to (2c) at 15 mol % in total, and the compound represented by Formula (3) at 18 mol % in total. This compound also contained the compound corresponding to Formula (1a') at 5 mol %. The ratio between the respective compounds was determined in the same manner as in the HPLC analysis method used in the synthesis of bis(2,3-bis(tert-butylmethylphosphino)quinoxaline)gold(I) chloride disclosed in the Example 1.

$^{31}$P-NMR (CDCl$_3$); 7.6-9.6 (m), 10.2 (s), 11.6-13.1 (m), 13.6 (s), 14.6-15.9 (m)

Comparative Example 1

(2) Synthesis of (R,R)-2,3-bis(tert-butylmethylphosphino)quinoxaline

According to the disclosure of Example 1 in JP-A-2007-56007 relating to the previous application of the present applicant, (R,R)-2,3-bis(tert-butylmethylphosphino) quinoxaline was obtained.

(2) Synthesis of bis(2,3-bis(tert-butylmethylphosphino)quinoxaline)gold(I) chloride Bis(2,3-bis(tert-butylmethylphosphino)quinoxaline)gold (I) chloride was obtained in the same manner as in the step (2) of Example 1, except that (R,R)-2,3-bis(tert-butylmethylphosphino)quinoxaline was used. This compound was constituted with the compound represented by Formula (1a').

$^{31}$P-NMR (CDCl$_3$); 13.6

$[\alpha]^D$=+195.3 (c=0.5, methanol, 25° C.)

Evaluation

In the following manner, the phosphine transition metal complexes obtained in the examples and the comparative examples were subjected to an in vitro anti-tumor activity test and to a test for toxicity caused when the complexes are orally administered to rats. The results are shown in the following Table 1.

[In Vitro Anti-Tumor Activity Test]

The phosphine transition metal complexes obtained in the examples and the comparative examples were subjected to an in vitro anti-tumor activity test. Specifically, KB (oral squamous cell carcinoma) and A375 (malignant melanoma) were used as cancer cells, and these cells were cultured in an incubator at 37° C. in a culture medium (RPMI-1640 or DEME) to which 10% inactivated fetal calf serum, L-glutamine, sodium pyruvate, 1×10$^5$ U/L of penicillin, and 100 mg/L of streptomycin had been supplemented. The cells were added such that each well contained 2×10$^5$ cells. Subsequently, the phosphine transition metal complex dissolved in dimethylsulfoxide was added to the medium and cultured for 48 hours. After the 48 hours of culture, a 5 mg/ml (3,[4,5-dimethylthiazol-2-yl]-2,5-diphenyltetrazolium bromide MTT) solution was added at 20 μl to each well, followed by culture for 3 to 4 hours in an incubator. Thereafter, 100 μl of a solution was further added to each well to completely solubilize the generated formazan crystals. The absorbance of the resultant at 492 nm was then measured, and IC$_{50}$ was calculated.

[Toxicity Test]

Toxicity caused when the phosphine transition metal complexes obtained in the examples and the comparative examples were orally administered to rats was tested. Specifically, male and female KM rats were quarantined and raised while being acclimated, and then the selected 20 rats in total including 10 male rats and 10 female rats were formed into a group. The phosphine transition metal complexes obtained in the examples and comparative examples were orally administered once to rats which were fasted over night before the administration and whose weights were recorded, by using corn oil as a solvent and with a design such that a group showing sufficient fatal cases was included to determine LD$_{50}$. The rats were observed at 10 minutes, 30 minutes, 1 hour, 2 hours, and 4 hours after the administration, and then observed every day to the fourteenth day, and a lethal dose 50% ($LD_{50}$) was calculated from the survival rate of the rats.

TABLE 1

| | Molar ratio of ligand | Ratio of generated gold complex (molar ratio) | | | | In vitro anti-tumor activity IC50 (μg/ml) | | Oral administration |
|---|---|---|---|---|---|---|---|---|
| | Racemic isomers:Meso isomer | (1a)-(1d) | (2a)-(2c) | (3) | (1a') | KB | A375 | LD50 (mg/kg) |
| Example 1 | 52:48 | 54 | 16 | 22 | 8 | 0.94 | 1.13 | 134.37 |
| Example 2 | 54:46 | 60 | 9 | 26 | 5 | 1.03 | 1.94 | 97.44 |
| Example 3 | 44:56 | 62 | 15 | 18 | 5 | 0.97 | 1.22 | 118.66 |
| Comparative Example 1 | 100:0 | 0 | 0 | 0 | 100 | 1.11 | 2.26 | 90.99 |

From the results shown in Table 1, it was confirmed that the anti-cancer agent containing the phosphine transition metal complex of the present invention has a higher anti-cancer activity and lower toxicity compared to the anti-cancer agent in the related art.

The invention claimed is:
1. An anti-cancer agent comprising:
   at least one kind of phosphine transition metal complex selected from a group of compounds represented by Formulae (1a) to (1d),
   at least one kind of phosphine transition metal complex selected from a group of compounds represented by Formulae (2a) to (2c),

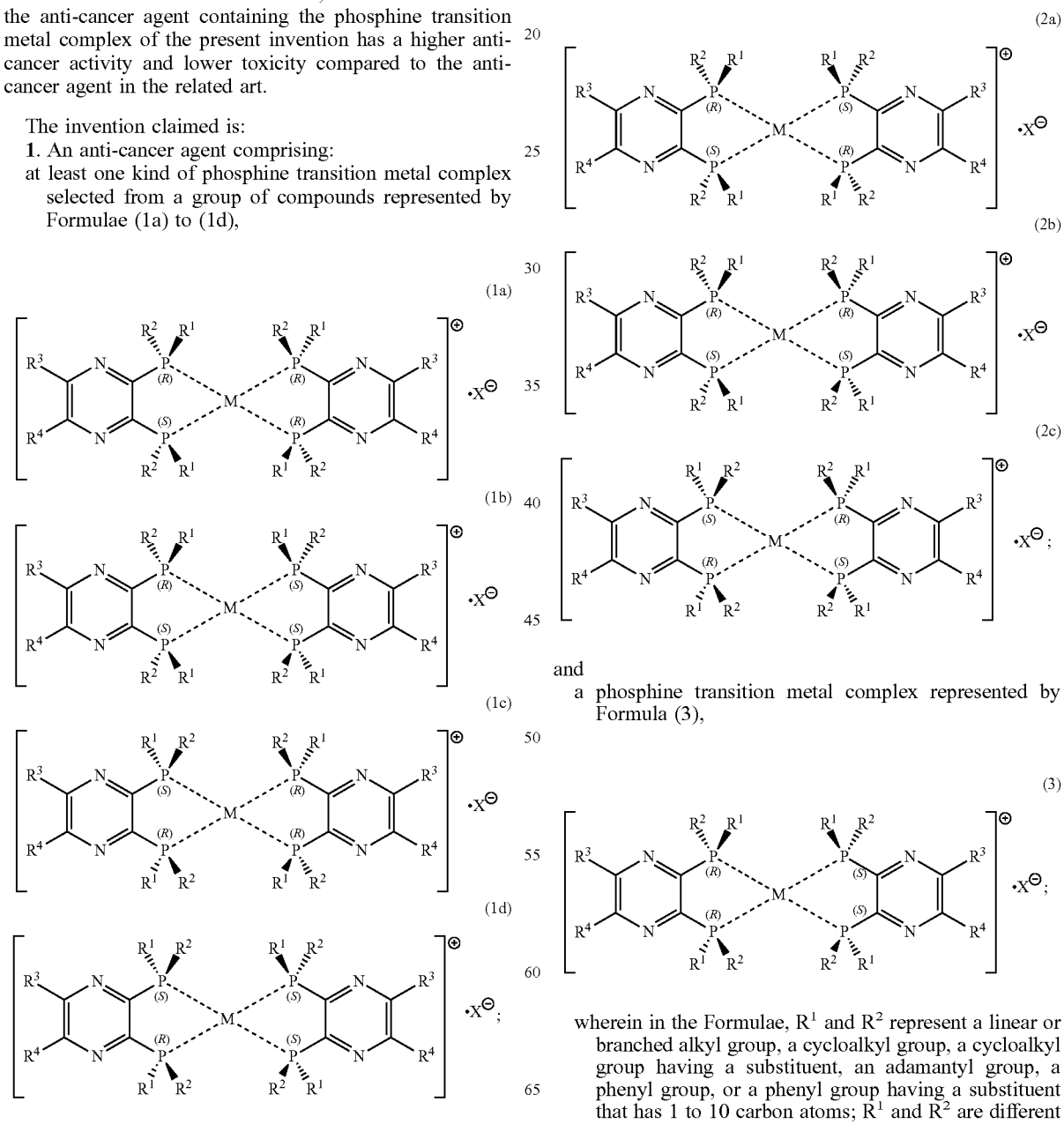

and
a phosphine transition metal complex represented by Formula (3), wherein in the Formulae, $R^1$ and $R^2$ represent a linear or branched alkyl group, a cycloalkyl group, a cycloalkyl group having a substituent, an adamantyl group, a phenyl group, or a phenyl group having a substituent that has 1 to 10 carbon atoms; $R^1$ and $R^2$ are different from each other, and $R^1$ has a higher priority than $R^2$ as ranked according to RS notation; $R^3$ and $R^4$ represent a hydrogen atom or a linear or branched alkyl group having 1 to 6 carbon atoms, and may be groups that are the same as or different from each other; $R^3$ and $R^4$ may form a saturated or unsaturated ring by binding to each other, and the saturated or unsaturated ring may have a substituent; M represents an atom of a transition metal selected from a group consisting of gold, copper, and silver; and $X^-$ represents an anion; and wherein the mixing ratio (molar ratio) among the total amount of the compounds represented by Formulae (1a) to (1d), the total amount of the compounds represented by Formulae (2a) to (2c), and the compound represented by Formula (3) is Formulae (1a) to (1d): Formulae (2a) to (2c):Formula (3)=20 to 80:10 to 30:10 to 80.

2. An anti-cancer agent comprising:

at least one kind of phosphine transition metal complex selected from a group of compounds represented by Formulae (1a) to (1d),

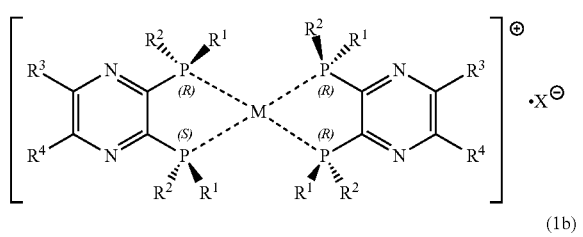

(1a)

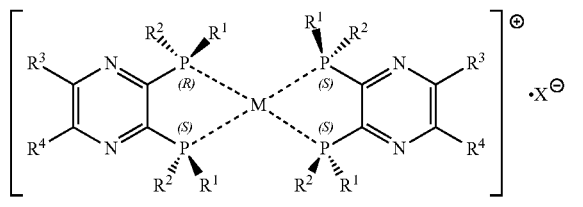

(1b)

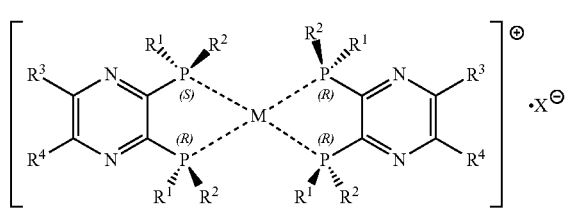

(1c)

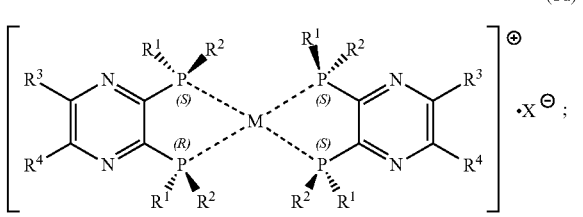

(1d)

at least one kind of phosphine transition metal complex selected from a group of compounds represented by Formulae (2a) to (2c),

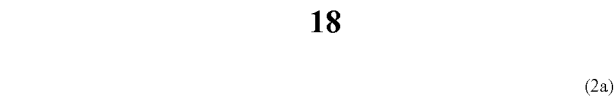

(2a)

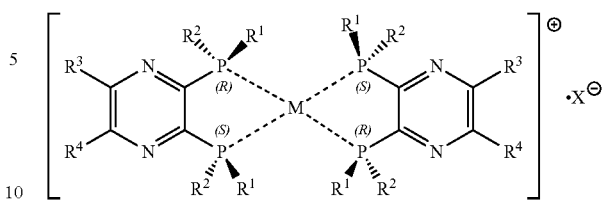

(2b)

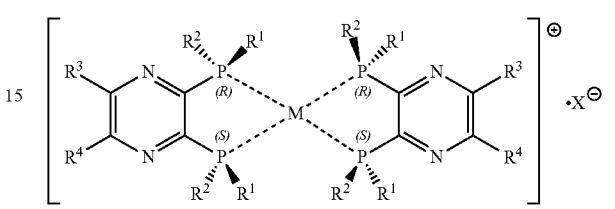

(2c)

and a phosphine transition metal complex represented by Formula (3),

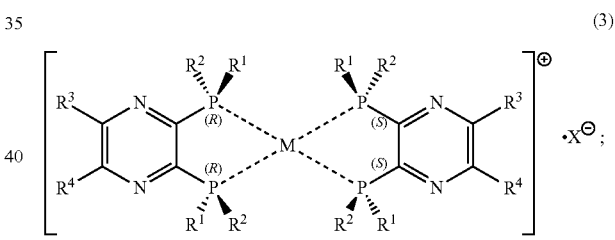

(3)

wherein in the Formulae, $R^1$ and $R^2$ represent a linear or branched alkyl group, a cycloalkyl group, a cycloalkyl group having a substituent, an adamantyl group, a phenyl group, or a phenyl group having a substituent that has 1 to 10 carbon atoms; $R^1$ and $R^2$ are different from each other, and $R^1$ has a higher priority than $R^2$ as ranked according to RS notation; $R^3$ and $R^4$ represent a hydrogen atom or a linear or branched alkyl group having 1 to 6 carbon atoms, and may be groups that are the same as or different from each other; $R^3$ and $R^4$ may form a saturated or unsaturated ring by binding to each other, and the saturated or unsaturated ring may have a substituent; M represents an atom of a transition metal selected from a group consisting of gold, copper, and silver; and $X^-$ represents an anion; and wherein the mixing ratio (molar ratio) among the total amount of the compounds represented by Formulae (1a) to (1d), the total amount of the compounds represented by Formulae (2a) to (2c), and the compound represented by Formula (3) is Formulae (1a) to (1d): Formulae (2a) to (2c):Formula (3)=40 to 70:5 to 25:15 to 50.

* * * * *